United States Patent

Amberg et al.

[11] Patent Number: 5,886,147
[45] Date of Patent: Mar. 23, 1999

[54] COMPOUNDS USEFUL FOR THE SYNTHESIS OF DOLASTATIN ANALOGS

[75] Inventors: Wilhelm Amberg, Friedrichsdorf; Harald Bernard, Bad Dürkheim; Ernst Buschmann, Ludwigshafen; Andreas Haupt, Schwetzingen; Lothar Janitschke, Kleinniedesheim; Bernd Janssen; Ulrich Karl, both of Ludwigshafen; Andreas Kling, Mannheim; Stefan Müller, Speyer; Bernd de Potzolli, Bad Dürkheim; Kurt Ritter, Heidelberg; Marco Thyes, Ludwigshafen; Thomas Zierke, Böhl-Iggelheim, all of Germany

[73] Assignee: BASF Aktiengesellschaft, Ludwigshafen, Germany

[21] Appl. No.: 737,279

[22] PCT Filed: Apr. 26, 1995

[86] PCT No.: PCT/EP95/01576

§ 371 Date: Nov. 6, 1996

§ 102(e) Date: Nov. 6, 1996

[87] PCT Pub. No.: WO95/30690

PCT Pub. Date: Nov. 16, 1995

[30] Foreign Application Priority Data

May 6, 1994 [DE] Germany ............... 44 15 998.6

[51] Int. Cl.⁶ .................................. C07K 1/02
[52] U.S. Cl. ................. 530/338; 530/331; 530/333
[58] Field of Search ............. 514/18, 19; 530/331, 530/333

[56] References Cited

U.S. PATENT DOCUMENTS 4,879,278  11/1989  Pettit et al. ............... 514/17
4,978,744  12/1990  Pettit et al. ............... 530/330

FOREIGN PATENT DOCUMENTS

93/23424  11/1993  WIPO .

OTHER PUBLICATIONS

J. Am. Chem. Soc., 1991, vol. 113, pp. 6692–6693.
The Chem. Synth. of Peptides, 1991, pp. 47–51.
Zaoral et al., Coll. Czech. Chem. Commun., vol. 27, 1962, pp. 1273–1277.
J. Org. Chem., vol. 52, 1987, pp. 2364–2367.
Tetrahedron, vol. 49, No. 4, Jan. 29, 1993, pp. 1913–1924.

Primary Examiner—Robert J. Hill, Jr.
Assistant Examiner—David Lukton
Attorney, Agent, or Firm—Keil & Weinkauf

[57] ABSTRACT

Compounds of the formula

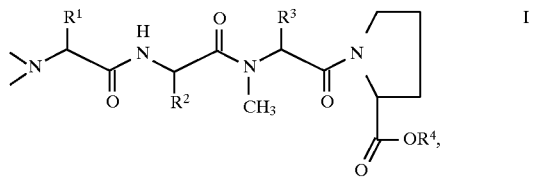

where $R^1$, $R^2$, $R^3$ and $R^4$ have the meaning stated in the description, and a process for preparing them are described. The compounds are suitable as starting material for synthesizing substances which are active against tumors.

1 Claim, No Drawings

COMPOUNDS USEFUL FOR THE SYNTHESIS OF DOLASTATIN ANALOGS

The present invention relates to novel tetrapeptides, their preparation and use.

BACKGROUND OF THE INVENTION

Dolastatin 15 is a substance which is described in U.S. Pat. No. 4,879,278 and has the following formula.

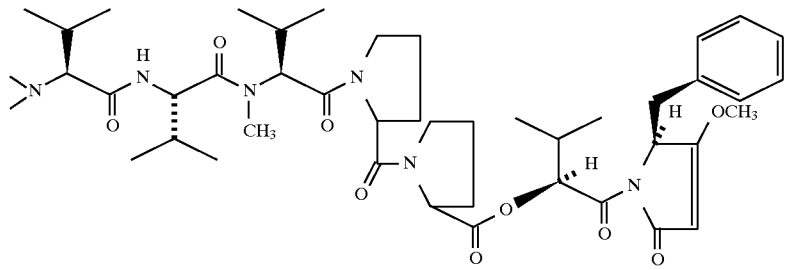

Dolastatin 15 is attracting great interest because of its great efficacy against various tumors. Its isolation from the lumpfish which is difficult to obtain is lengthy and time-consuming, and the process provides the active substance in moderate yield and poorly reproducible quality. In order to make the active substance available in gram quantities for animal experiments, Pettit et al. (J. Am. Chem. Soc. 113 [1991] 6692–6693) have developed a synthetic method. The central intermediate in this is the tetrapeptide of the formula Ia

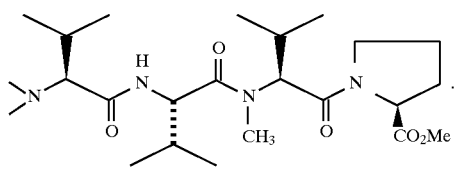

WO 93/23424 describes antineoplastic active substances whose effect exceeds that of dolastatin 15. Many active substances in WO 93/23424 can be prepared from tetrapeptides of the formula I

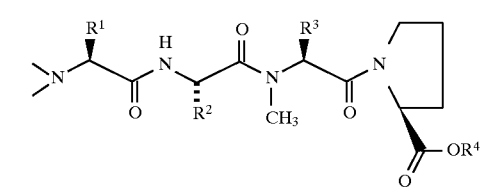

where $R^1$–$R^4$ are $C_1$–$C_6$-alkyl groups.

In order to make the peptides of WO 93/23424 and dolastatin 15 available in sufficient quantity for clinical tests it was necessary to find a process for preparing the tetrapeptides I which can be implemented industrially.

The solid-phase synthesis described in WO 93/23424 is unsuitable for preparing large amounts of product. It provides impure product which requires laborious chromatographic purification.

Pettit et al. (J. Am. Chem. Soc. 113 [1991] 6692–6693) describe an elegant laboratory synthesis for Ia. This entails the tripeptide Val—MeVal—Pro—OMe being reacted with

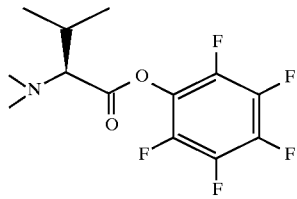

(Short name: $Me_2Val$—OPfp) to give the tetrapeptide Ia.

The synthesis of $Me_2Val$—OPfp takes place according to Pettit et al. (U.S. Pat. 4,978,744) as follows:

Initially valine is dimethylated on the nitrogen. The resulting dimethylvaline must be reacted with a condensing agent and pentafluorophenol (HO-Pfp).

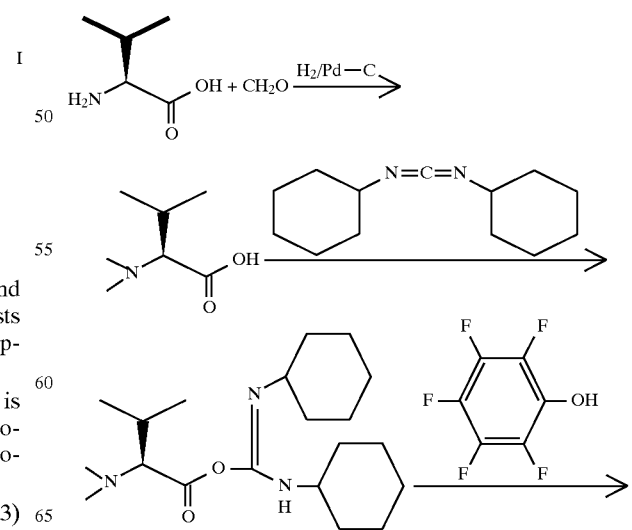

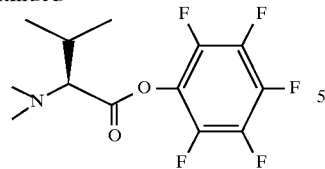

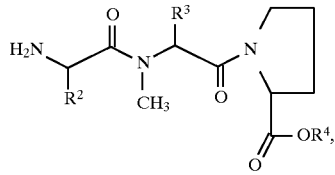

where $R^2$, $R^3$ and $R^4$ have the abovementioned meaning, with an amino acid of the formula III $$R^1\text{—CH(NHZ)—COOH} \quad\quad\quad\quad III,$$

where $R^1$ has the abovementioned meaning, and Z is a benzyloxycarbonyl protective group which may be substituted on the phenyl ring, and dimethylating the resulting compound on the $NH_2$ group.

DESCRIPTION OF THE PREFERRED EMBODIMENTS

In the formula I, $R^1$, $R^2$ and $R^3$, which are identical or different, are preferably ethyl, n-propyl, isopropyl, t-butyl, sec-butyl, 2-methylbutyl or 3-methylbutyl. $R^4$ is preferably methyl or ethyl.

The amino acids in the tetrapeptide preferably have the L configuration.

The coupling reaction of II with III can be carried out, for example, by the mixed anhydride method (see Houben-Weyl, Volume XV/2, 1974; J. Am. Chem. Soc. 74 [1952] 676; Coll. Czechoslov. Chem. Comm. 27 [1962] 1273). The carbonyl chlorides (preferably pivaloyl chloride, 2-ethylbutyryl chloride, isovaleryl chloride) or chloroformic esters (the methyl, ethyl, isopropyl, isobutyl, phenyl, chloroethyl and trichloromethyl esters are preferably employed) used as coupling reagents can be obtained in industrial quantities and are also very suitable for syntheses on the industrial scale. It is particularly advantageous that the couplings according to the invention take place without racemization.

Suitable solvents are tetrahydrofuran, dioxane, acetonitrile, dimethyl sulfoxide, ethyl acetate, dimethylformamide, methylene chloride, toluene, N-methylpyrrolidone and mixtures thereof. Methylene chloride, toluene and mixtures thereof are preferred. Particularly suitable bases for the reaction are: triethylamine, tributylamine, N-ethylpiperidine, diisopropylethylamine and N-methylmorpholine; triethylamine and N-methylmorpholine are preferred.

The reaction is carried out at from $-40°$ C. to $+30°$ C., preferably from $-15°$ C. to $+15°$ C.

The invention also relates to the compounds of the formula I where, however, $R^1$, $R^2$ and $R^3$ are not all isopropyl radicals when $R^4$ is a methyl group, and to the salts thereof with various acids.

Examples of acids which may be mentioned are: hydrochloric acid, citric acid, tartaric acid, lactic acid, phosphoric acid, methanesulfonic acid, acetic acid, formic acid, maleic acid, fumaric acid, malonic acid, succinic acid, malic acid, sulfuric acid, benzoic acid and oxalic acid.

The compounds of the formula I are very suitable for preparing dolastatin 15 and numerous compounds described in WO 93/23424 (cf. Examples 214–246 and others).

The conventional three-letter code is used to abbreviate the amino acids. $Me_2Val$ means N,N-dimethyl-L-valine, MeVal means N-methylvaline, Me means methyl, tert-Leu means tertiary Leucine (HOOC—CH($NH_2$)—C($CH_3$)$_3$), This process is very troublesome owing to the large number of reaction steps required. An additional factor is that pentafluorophenol is a very costly reagent which is unavailable in sufficient quantity for industrial syntheses. In addition, its use leads to fluorine-containing wastes which can be disposed of only with difficulty and possibly with formation of dioxins.

The use of condensing agents in the synthesis also leads to problems. Thus, it is known that handling dicyclohexylcarbodiimide may lead to sensitization and extremely severe allergic reactions. Workup of the batches produces the corresponding urea which can be removed from the product only laboriously and often only incompletely. Carbodiimides which, like N-ethyl-N'-dimethylaminopropylcarbodiimide, react to form water-soluble ureas are extremely costly and are not available in industrial quantities.

Replacement of pentafluorophenol/carbodiimide by pentafluorophenyl trifluoroacetate or its carbonates, eg. pentafluorophenyl 1,2,2,2-tetrachloroethyl carbonate (J. Org. Chem. 52 [1987] 2364) also provides no advantages.

Racemization occurs in active ester formation and peptide coupling and represents a serious problem in this method (see J. Jones: The Chemical Synthesis of Peptides, Oxford 1991, page 57).

Another published method for linking dimethylvaline to other amino acids (T. Shioiri et al.: Tetrahedron 49 [1993] 1913–1924), which uses diethylphosphoryl cyanide (DEPC) as coupling reagent, likewise involves serious disadvantages: DEPC is very costly, not obtainable in large quantity, corrosive and very toxic. The cyanide-containing mother liquors and washings must be disposed of as special waste.

SUMMARY OF THE INVENTION

The present invention relates to a process for preparing the tetrapeptides I, which makes use of intermediates which are available in large quantities, and which can be carried out without out racemization and without environmental hazard.

The invention relates to a process for preparing compounds of the formula

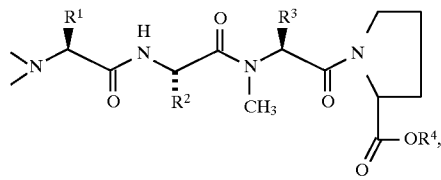

where $R^1$, $R^2$, $R^3$ and $R^4$ are identical or different and are each $C_{1-6}$-alkyl, which comprises condensing a compound of the formula II Me₂ tert-Leu means N,N-dimethyltertiary-leucine and Me tert-Bu-Ala means N-methyl-tertiarybutylalanine (HOOC—CH(NHCH₃)—CH₂—C(CH₃)₃), Hyp means 4-hydroxyproline, Bu means n-butyl, tBu means tertiary butyl, Hx means n-hexyl and Et means ethyl.

EXAMPLES

EXAMPLE 1

Preparation of Z-Val-Val-MeVal-Pro-OMe 17.84 kg (70.88 mol) of Z-valine and 4.59 kg (74.42 mol) of triethylamine were dissolved in 170 l of methylene chloride in a 400 l vessel. To this solution were added at −5° to −10° C. 8.58 kg (70.88 mol) of pivaloyl chloride. After a reaction time of 2 h at −5° C., a solution of 24.2 kg of Val-MeVal-Pro-OMe in 86 l of methylene chloride was run in at −5° C. After a further 2 h at −5° C., the mixture was heated to 20° C. and stirred at this temperature for 12 h. 50 l of water were added for working up. After removal of the aqueous phase, the organic phase was extracted once with 40 l of 2N hydrochloric acid and twice with 40 l of 2N sodium hydroxide solution each time. The organic phase was washed until neutral and then the methylene chloride solvent was removed by distillation and replaced by 300 l of diisopropyl ether. The product was crystallized by heating the emulsion of the oily product to 60° C., adding seed crystals and keeping at 60° C. for 7 h. To complete the crystallization, the mixture was stirred further at 50° C. for 5 h and then at 40° C. for 5 h and subsequently cooled to 20° C. The suspension of crystals was discharged through a 120 l pressure filter.

Yield: 32.2 kg ≙79% of theory

Purity: 98.5% (HPLC percentage area)

Melting point: 134°–135° C.

EXAMPLE 2

Preparation of Me₂Val-Val-MeVal-Pro-OMe×HCl 20 kg (34.8 mol) of Z-Val-Val-MeVal-Pro-OMe were introduced together with 2 kg of 5% palladium/carbon into 200 l of methanol in a 400 l hydrogenation vessel. Then, while cooling, hydrogen was passed in at 20° C. until precursor was no longer detectable in the reaction solution. Subsequently 8.46 kg of 37% strength (104 mol) formalin solution were added, and hydrogenation was continued at 20° C. until hydrogen uptake ceased. The catalyst was filtered off as the contents of the vessel were discharged. The filtrate was worked up by concentrating to 50 l in a 400 l enameled vessel under waterpump vacuum. Then 200 l of isopropanol were added, and the mixture was again concentrated to 50 l. The residue was then dissolved in 135 l of methyl tert-butyl ether, and one equivalent of isopropanolic HCl was added while cooling at 20° C. The resulting suspension of crystals was stirred further at 20° C. for 3–4 h and at 0°–5° C. for 2 h and then filtered through a 120 l pressure filter. The filter cake was washed once with 50 l of fresh methyl tert-butyl ether.

Yield: 16.2 kg ≙92.3% of theory

Purity: 99.9% (HPLC percentage area)

Melting point: 224° C. (decomposition)

EXAMPLE 3

It was also possible to isolate the intermediates Val-Val-MeVal-Pro-OMe when workup was carried out as follows after the first hydrogenation stage:

The reaction solution was separated from the catalyst and concentrated. The residue was taken up in ethyl acetate. The ethyl acetate solution was extracted twice with 2N hydrochloric acid. The acidic aqueous phase was adjusted to pH 9 with sodium hydroxide solution and extracted twice with methylene chloride. The methylene chloride phase was then washed until neutral and evaporated.

HPLC 96.8%

1H-NMR (400 MHz, CDCl₃/ TMSint.): δ (ppm): 0.84–1.08 (m, 18H); 1.45–1.6 (s, wide, NH₂); 1.85–2.15 (m, 4H); 2.18–2.38 (m, 3H); 3.15 (s, N—CH₃); 3.25 (d, 1H); 3.65–3.75 (m, 1H); 3.73 (s, O—CH₃); 3.9–4.05 (m, 1H); 4.38–4.45 (m, 1H); 4.73–4.83 (m, 1H); 5.12 (d, 1H); 7.9 (d, NH)

EXAMPLE 4

Me₂Val-Val-MeVal-Pro-OMe×HCl can also be prepared by the following method which dispenses with isolation and purification of the intermediate Z-Val-Val-MeVal-Pro-OMe 128 g (0.51 mol) of Z-valine (purity: 99.8%) and 55.1 g (0.54 mol) of triethylamine (purity: 99%) were dissolved in 1.2 l of methylene chloride in a 4 l flask. 62.1 g (0.51 mol) of pivaloyl chloride (purity: 99%) were added to this solution at −5° C. to −10° C. After a reaction time of 2 h at −5° C., a solution of 174.6 g (0.51 mol) of Val-MeVal-Pro-OMe in 0.8 l of methylene chloride was run in, and the mixture was stirred at −5° C. for a further 2 h and then, after warming to 20° C., for a further 12 h. 370 ml of water were then added to the mixture. After phase separation, the methylene chloride phase was washed once with 290 ml of 2N hydrochloric acid, twice with 290 ml of 2N sodium hydroxide solution each time and three times with 370 ml of water. The methylene chloride was subsequently evaporated off and replaced by 3 l of methanol. To this solution was added a suspension of 30 g of 5% palladium/carbon in 110 ml of water and hydrogenation was carried out at 25° C. using a gas-introduction stirrer and hydrogen burette until one equivalent of hydrogen had been taken up. Then 123 g (1.53 mol) of 37% strength formalin solution were added and hydrogenation was carried out until a further 2 equivalents of hydrogen had been taken up. The catalyst was then removed and the solution was evaporated in a rotary evaporator. The remaining oil was dissolved in 670 ml of isopropanol and 2.6 l of methyl tert-butyl ether. One equivalent of isopropanolic HCl was added to this solution. The resulting suspension of crystals was stirred at 20° C. for a further 12 h and then filtered with suction. The filter cake was washed with a little fresh methyl tert-butyl ether and subsequently dried at 40° C. under reduced pressure.

Yield: 182.8 g ≙71% of theory

Purity: 99.4% (HPLC percentage area) Melting point: 224° C. (decomposition)

The following can be prepared in a similar way to Examples 1 to 4:

| | |
|---|---|
| 5 | Me₂Val-Val-MeValPro-OEt |
| 6 | Me₂Ile-Ile-MeVal-Pro-OMe |
| 7 | Me₂Val-tert.Leu-MeVal-Pro-OtBu |
| 8 | Me₂Val-Leu-MeVal-Pro-OMe |
| 9 | Me₂Leu-Val-MeVal-Pro-OEt |
| 10 | Me₂tert.Leu-Val-MeVal-Pro-OBu |
| 11 | Me₂Val-tert.Leu-MeVal-Pro-OtBu |
| 12 | Me₂tert.Leu-tert.Leu-MeVal-Pro-OHx |
| 13 | Me₂Leu-Val-MeVal-Pro-OEt |
| 14 | Me₂Val-Val-Metert.Leu-Pro-OEt |
| 15 | Me₂Val-Val-Metert.BuAla-Pro-OHx |
| 16 | Me₂Val-tert.Leu-MeVal-Pro-OMe |

| | |
|---|---|
| 17 | Me₂Val-Ile-MeVal-Pro-OEt |
| 18 | Me₂tert.Leu-Val-Metert.Leu-Pro-OtBu |

Use Examples

Preperation of Me₂Val-Val-MeVal-Pro-Pro-NHBzl× HCl 15.9 g (31.5 mol) of Me₂Val-Val-MeVal-Pro-OMe×HCl (purity: 99.5%) were introduced together with 140 l of toluene and 15 l of methanol into a 400 l vessel. To this were added 3.15 kg (76.38 mol) of sodium hydroxide pellets. After hydrolysis was complete, ie. after about 3 h at 20° C., the mixture was neutralized by adding isopropanolic HCl. It was subsequently azeotropically distilled with toluene under 100 mbar until free of alcohol and water. The volume of solvent which was distilled off was successively replaced by toluene. Subsequently, 80 l of methylene chloride and 6.44 kg (63.0 mol) of triethylamine were added, the mixture was cooled to −5° C. and, at this temperature, 3.84 kg (31.5 mol) of pivaloyl chloride were metered in. After reaction for 2 hours, 7.6 kg (31.5 mol) of Pro-NHBzl×HCl were added a little at a time at −50° C. to 0° C. After the mixture had stood at −5° C. for 2 h it was warmed to 20° C. and left to react for a further 6 h. Subsequently the added methylene chloride was removed by distillation under 500 mbar, and 80 l of toluene were added. Then 50 l of water were added and the pH of the aqueous phase was adjusted to pH 9. After vigorous stirring, the aqueous phase was separated off, and the organic phase was subsequently washed once with 25 l of water. The organic phase was subsequently extracted twice with 50 l of 2N hydrochloric acid each time. The product was back-extracted from the acidic aqueous phase after adjustment of the pH to 9 by extraction 3 times with 50 l of methylene chloride each time. After the methylene chloride phase had been washed until neutral, the methylene chloride was removed by distillation and replaced by 180 l of methyl ethyl ketone. The solution was warmed to 40° C. and one equivalent (31.5 mol) of isopropanolic HCl was added. The resulting suspension was warmed to 60° C. and subsequently stirred for 12 h. It was then cooled to 20° C. and stirred for a further 5 h. It was subsequently cooled to 5° C. and filtered through a 120 l pressure filter. The filter cake was washed with 60 l of fresh methyl ethyl ketone at 5° C. After initial drying on the filter, the product was dried to constant weight in a vacuum oven at 40° C.

Yield: 14.36 kg ≙67% of theory

Purity: 99.6% (HPLC percentage area)

Melting point: 214° C. (decomposition)

The following can be prepared in a similar way to the use example:

Me₂Val — Val — MeVal — Pro — Pro — Val — Phe
Me₂Ile — Ile — MeVal — Pro — Pro — Val — Phe — NH₂
Me₂Val-tert.Leu — MeVal — Pro — Pro — Val — Phe — NH₂
Me₂Val — Leu — MeVal — Pro — Pro — Val — Phe — NH₂
Me₂Leu — Val — MeVal — Pro — Pro — Val — Phe — NH₂

Me₂tert.Leu — Val — MeVal — Pro — Pro — Val — Phe — NH₂
Me₂tert.Leu — Val — MeVal — Pro — Pro — Val — NH₂
Me₂Val-tert.Leu — MeVal — Pro — Pro — Val — NH₂
Me₂tert.Leu-tert.Leu — MeVal — Pro — Pro — NH₂
Me₂Leu — Val — MeVal — Pro — Pro — Val — Phe — NH₂

Me₂Val — Val — Metert.Leu — Pro — Pro — Val — Phe — NH₂
Me₂Val — Val — Metert.BuAla — Pro — Pro — Val — Phe — NH₂
Me₂Val-tert.Leu — MeVal — Pro — Pro — Val — Phe — NH₂
Me₂Val — Leu — MeVal — Pro — Pro — Val — Phe — NH₂
Me₂Val — Ile — MeVal — Pro — Pro — Val — Phe — NH₂

We claim:

1. A process for preparing a compound of formula I

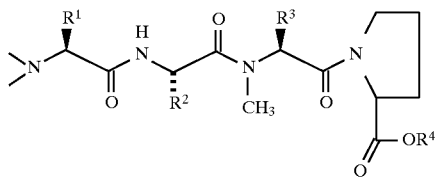

wherein

R¹, R², R³ and R⁴ are identical or different and are each C₁₋₆-alkyl;

which process comprises:

(a) condensing a compound of formula II

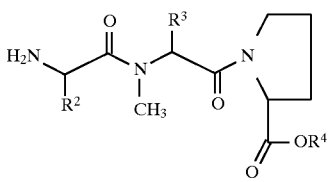

where

R², R³ and R⁴ have the above mentioned meaning, with an amino acid of formula III

where R¹ has the above mentioned meaning, and Z is a benzyloxycarbonyl protective group optionally substituted on the phenyl ring;

(b) removing said protective group; and (c) dimethylating the N-terminal amino group of the resulting compound.

* * * * *